(12) United States Patent
Zepic et al.

(10) Patent No.: US 7,381,018 B2
(45) Date of Patent: Jun. 3, 2008

(54) TOOL CHUCK

(75) Inventors: Janez Zepic, Ljubljana (SI); Bostjan Podlipec, Vrhnika (SI)

(73) Assignee: LPKF Laser & Elektronika D.O.O., Zgornje Jezersko (SI)

( * ) Notice: Subject to any disclaimer, the term of this patent is extended or adjusted under 35 U.S.C. 154(b) by 233 days.

(21) Appl. No.: 11/328,837

(22) Filed: Jan. 10, 2006

(65) Prior Publication Data

US 2007/0003385 A1    Jan. 4, 2007

(30) Foreign Application Priority Data

Jan. 11, 2005    (DE) ............... 10 2005 001 368

(51) Int. Cl.
*B23C 9/00*    (2006.01)
*B23B 5/22*    (2006.01)
(52) U.S. Cl. ............ 409/234; 409/231; 408/141; 408/240; 279/50; 279/74
(58) Field of Classification Search ........ 409/234, 409/233, 232, 231; 408/141, 238, 239 R, 408/240; 279/50, 57, 74, 134, 135, 142
See application file for complete search history.

(56) References Cited

U.S. PATENT DOCUMENTS

| | | | | |
|---|---|---|---|---|
| 2,370,729 A | * | 3/1945 | Hoppe | .......... 279/50 |
| 2,466,651 A | * | 4/1949 | Zagar | .......... 279/50 |
| 2,655,826 A | * | 10/1953 | Goldsby | .......... 279/50 |
| 4,874,314 A | | 10/1989 | Fleer et al. | |
| 5,997,225 A | * | 12/1999 | Young et al. | .......... 409/182 |
| 6,045,306 A | * | 4/2000 | Buddendeck et al. | ....... 409/182 |
| 6,155,826 A | | 12/2000 | Howard | |
| 6,244,798 B1 | | 6/2001 | Podlipec et al. | |
| 6,315,507 B1 | * | 11/2001 | Podlipec et al. | .......... 409/234 |
| 6,988,734 B2 | * | 1/2006 | Zierpka | .......... 408/240 |

FOREIGN PATENT DOCUMENTS

| | | |
|---|---|---|
| DE | 40 30 176 | 3/1992 |
| DE | 197 09 136 | 9/1998 |
| DE | 197 48 735 | 5/1999 |
| DE | 103 45 993 | 5/2005 |
| EP | 1 232 731 | 8/2002 |

OTHER PUBLICATIONS

European Search report for patent application EP 06 00 0124, mailed Jun. 22, 2006.

* cited by examiner

*Primary Examiner*—Dana Ross
(74) *Attorney, Agent, or Firm*—Darby & Darby

(57) ABSTRACT

The invention relates to a tool holder 1 for a rotating tool, especially a drilling head and/or milling head, comprising a drive shaft 4 that can be connected to a drive motor and a collet chuck 2 that is non-rotatably connected to the drive shaft 4 in order to hold the tool, whereby the drive shaft 4 and the collet chuck 2 are positively connected by means of a coupling element 5 for purposes of transmitting torque. In order to securely hold the tool and to concurrently have a simple construction of the tool holder 1, it is proposed for the coupling element 5 to be axially displaceable relative to the collet chuck 2 so as to release the tool.

24 Claims, 6 Drawing Sheets

TOOL CHUCK

The invention relates to a tool holder for a rotating tool, especially a drilling head and/or milling head, comprising a drive shaft that can be connected to a drive motor and a collet chuck that is non-rotatably connected to the drive shaft in order to hold the tool, whereby the drive shaft and the collet chuck are positively connected by means of a coupling element for purposes of transmitting torque.

BACKGROUND

Such a tool holder is known from German patent application DE 197 48 785 A1 as a drilling head and/or milling head having a collet chuck that can be actuated by means of a quick-release mechanism, whereby the collet chuck is connected in one piece to a drive shaft, so as to form a single part. The drive shaft and, with it, the collet chuck can, be displaced axially by means of a lever, namely, in a split taper sleeve that is secured in the axial direction. The axial displacement of the collet chuck in the split taper sleeve cancels out a non-positive engagement of gripper arms of the collet chuck and a conical inner surface of the split taper sleeve, as a result of which a tool held by the gripper arms is released.

Moreover, a dental handpiece having a grip chuck with a clamping bushing held in a spindle and a plunger that can be actuated by means of a pushbutton are known from U.S. Pat. No. 6,155,826. The actuation of the plunger, which is arranged on a central axis of the spindle and of the clamping bushing, can release a tool that is configured as a tooth drill and held in the clamping bushing.

SUMMARY OF THE INVENTION

Building upon the state of the art, an object of the present invention is to provide a tool holder that is capable of securely holding the tool and that has a simple construction.

The present invention provides a tool holder of the above-mentioned type in which the coupling element can be displaced axially relative to the collet chuck so as to release the tool.

According to the present invention, through the simple axial displacement of the coupling element relative to the collet chuck, the tool can be released and removed from the tool holder, for instance, at the end of a work procedure and/or in order to change the tool. Advantageously, the drive shaft and the collet chuck are constantly positively connected to each other via the coupling element, so that torque can be transmitted from the drive shaft to the collet chuck continuously, even while the tool is being loosened. Therefore, according to the invention, the coupling element fulfills a dual function, namely, on the one hand, the coupling element can loosen the tool held in the collet chuck while, on the other hand, the coupling element makes it possible to continuously transfer the motor output of the drive motor to the collet chuck and to the tool that is optionally held therein. Therefore, the tool holder can make do with relatively few parts and it is inexpensive to manufacture. Preferably, the drive shaft and the collet chuck are positively connected to each other by means of the coupling element, also for purposes of changing the tool, although here, it is also fundamentally conceivable to have a frictional connection. Since the position of the collet chuck that holds the tool is axially unchangeable and since the coupling element (and not the collet chuck) can be displaced axially, thus allowing the tool to be guided very precisely, the tool holder according to the invention is particularly well-suited for machine tools that are used to create fine structures, especially drilling and/or milling machines for printed circuit boards, engraving machines, 3D-machining equipment. Moreover, the tool holder is very wear-resistant and durable. The tool holder according to the invention also has the special advantage that its concentric running is highly precise. Furthermore, the invention advantageously achieves a very high pull-out force for the tool, for instance, a pull-out force in the order of magnitude of 500 N at a tool outer diameter of 3 mm (corresponding to a collet chuck inner diameter). In comparison to this, the collet chucks known from the state of the art, which additionally have the disadvantage that they require a very strong helical spring to exert a counterforce to the pull-out force, only achieve a pull-out force in the order of magnitude of about 100 N to 150 N. In contrast, the tool holder according to the invention is considerably lighter in weight and has a more compact construction and is more cost-efficient to produce and use; at the same time, the tool holder according to the invention is considerably more operationally reliable than the comparable tool holders known so far, and much less force is needed to open the collet chuck. Another major advantage of the invention lies in the fact that several functions are integrated into the collet chuck along the lines of a combination collet chuck, namely, on the one hand, the function of holding the tool and, on the other hand, the function of changing the tool and also the transmission of torque from the drive motor to the tool.

According to an advantageous refinement of the invention, the construction and production of the tool holder can be further simplified if the drive shaft and the coupling element are joined to each other so as to form a single part. Preferably, the drive shaft and the coupling element are configured in one piece.

The risk of damage to the collet chuck when tools are inserted into or removed from the collet chuck can advantageously be countered in that, according to another refinement of the invention, the end area of the collet chuck facing the drive shaft has a first inner diameter, and its end area facing away from the drive shaft has a second inner diameter that is larger than the first inner diameter. In this manner, the tool is held by the collet chuck in the end area of the collet chuck facing the drive shaft, that is to say, in an area facing away from a collet chuck opening on the side of the tool, thus resulting in a particularly stable and secure holding of the tool.

According to another advantageous refinement of the invention, the operational reliability of the tool holder can be additionally increased in that the coupling element has at least one coupling projection that engages with the collet chuck.

This advantageously results in an especially simple construction of the tool holder when, according to a refinement of the invention, the coupling projection has a wedge on its end facing the collet chuck. Here, it is particularly advantageous for the wedge to be configured continuously, so that it forms one single coupling projection and preferably extends completely beyond the diameter of the collet chuck. In this manner, a large engagement surface area for good force transmission and a very secure engagement with the collet chuck are achieved. Moreover, this makes it possible to easily finish the surface of the wedge precisely, for example, through polishing, which further increases the operational reliability.

According to another advantageous refinement of the invention, the coupling element has a centered recess on an end facing the collet chuck. Such a recess, which can be configured, for instance, as a pocket hole, offers the advantage that the tool can pass completely through the collet chuck and into this recess of the coupling element, so that, on the one hand, the guidance of the tool can be further improved and, on the other hand, the tool holder is also suitable to hold long tools while retaining its compact construction.

According to another advantageous refinement of the invention, the collet chuck has at least one axially oriented collet chuck slit and the coupling projection engages with the collet chuck slit. Thus, by displacing the coupling element with the coupling projection relative to the collet chuck slit, the collet chuck can easily be, for example, widened, thereby releasing the tool.

A tool holder whose dimensions are compact while its weight is low can be advantageously achieved in that, according to a refinement of the invention, the collet chuck slit forms an axial collet chuck opening on the end of the collet chuck facing the drive shaft.

According to an advantageous refinement of the invention, the spring properties of the collet chuck and thus the holding of the tool are improved in that the width of the collet chuck slit increases in a direction facing away from the drive shaft, that is to say, the slit widens in the direction facing away from the drive shaft.

The bearing of the drive shaft and of the collet chuck can be simplified and the concentric running of the tool can be further improved according to another advantageous refinement of the invention if a spindle shaft is provided that holds the drive shaft and the collet chuck.

In this context, the stability of the tool holder is advantageously additionally increased in that, according to a refinement of the invention, the collet chuck is arranged in a centered through-recess of the spindle shaft and lies against an axial stop of the spindle shaft.

According to an advantageous refinement of the invention, the running of the tool is further improved if the collet chuck is securely supported in the spindle shaft. Wear and tear to the collet chuck and to the spindle shaft are minimized as a result of the fact that the collet chuck is rigidly and securely arranged in the spindle shaft, especially in comparison to an axially displaceable arrangement of the collet chuck as is known from the state of the art.

In order to further increase the pull-out force of the tool, for instance, when milling is carried out at a low speed in aluminum, it is proposed according to an advantageous refinement of the invention that a screw be provided that locks the collet chuck relative to the spindle shaft.

According to another advantageous refinement of the invention, unintentional loosening of the tool during operation can be reliably avoided if a compression spring is provided that counteracts an axial displacement of the coupling element. With such an embodiment, it is nevertheless easy to release the tool, since all that is necessary to intentionally displace the coupling element axially is to overcome the resistance of the compression spring.

Moreover, according to another advantageous embodiment of the invention, a friction coupling is provided to transmit to the coupling element an axial force that brings about an axial displacement of the coupling element. As a result—since the collet chuck is opened by the axial displacement of the coupling element, and the force needed for this purpose is transmitted via a friction coupling—it is prevented that a rotating collet chuck and/or a rotating coupling element (optionally including the drive shaft) can become engaged with a non-rotating part during the opening, in other words, when the tool is being loosened. Thus, the tool holder is protected against damage in a simple manner, namely, especially when the motor is not switched off, which is a step that diverges from the normal operating procedure, that is to say, when the tool is changed, the drive motor is first switched off, then the actuation element (for instance, hand lever) is operated, thus opening the collet chuck and loosening the tool, and finally the tool is removed from the collet chuck and then the entire procedure is repeated in reverse order. Both the transmission of the axial force to the coupling element and the axial displacement of the coupling element are preferably completely independent of the motor drive, that is to say, of the transmission of torque from the drive motor to the tool.

It is fundamentally conceivable that friction elements of the friction coupling with their friction surfaces could be engaged radially. In contrast, particularly high forces can be reliably and continuously transmitted when, according to an advantageous embodiment of the invention, the friction coupling has a first friction element that is securely connected to the drive shaft and a second friction element that can be brought into contact with the first friction element and that is axially displaceable relative to the drive shaft. Moreover, in this embodiment, the friction coupling is very wear-resistant.

Undesired wear and tear when the friction coupling is in the non-operative state, that is to say, when the friction elements are operationally separated, can be advantageously prevented in that, according to a refinement of the invention, the first friction element and the second friction element are each supported on the tool side against a compression spring. In this manner, it can be ensured that the friction elements are at a distance from each other when they are in the non-operative state and are thus not subject to wear and tear.

According to another advantageous refinement of the invention, a manually operable actuation element, for example, a hand lever, is provided for the axial displacement of the coupling element. This allows the tool to be loosened in a simple manner and with a high level of operational reliability.

According to another advantageous embodiment of the invention, an actuation element that can be operated pneumatically or else by an electric motor or a hydromotor is provided for the axial displacement of the coupling element. This can be a hand lever with a recess with which a drive operated pneumatically or else by an electric motor or a hydromotor engages in order to actuate the lever.

Damage to the tool holder, especially due to the penetration of dirt, is reliably prevented according to an advantageous embodiment of the invention if an axially moveable sleeve is provided to cover a connecting joint area between the actuation element and the coupling element and/or the drive shaft.

According to another advantageous embodiment of the invention, the drive shaft has a coupling on the motor side that connects the drive shaft to a motor driven shaft and that is engaged irrespective of the axial displacement of the coupling element, so that, on the one hand, the coupling can minimize drive influences on the tool holder and, on the other hand, the tool can be changed without interrupting the transmission of torque from the drive motor. Preferably, the coupling can have a projection that can be secured to the motor driven shaft, for instance, with a screw, and that can be displaced axially, for example, relative to the motor driven shaft, as a result of which an axial position of the coupling can be functionally adjusted especially to the axial displaceability of the coupling element.

Contamination of the tool holder, for instance, due to flying chips, especially when a workpiece is being machined, can be reliably prevented in that, according to another advantageous refinement of the invention, a disk protruding radially to the outside is arranged on the collet chuck or on the spindle shaft in the end area of the collet chuck facing away from the drive shaft or in the end area of the spindle shaft facing away from the drive shaft. This disk prevents dirt particles from getting into the tool holder.

The disk is capable of performing its function particularly well and it is also highly durable if, according to an advantageous embodiment of the invention, the disk is made of polytetrafluoroethylene (PTFE).

BRIEF DESCRIPTION OF THE DRAWINGS

The invention allows numerous embodiments. In order to further elucidate its basic principle, several of these embodiments are shown schematically in the drawing and described below. The drawing shows the following.

DETAILED DESCRIPTION

Figure 1:
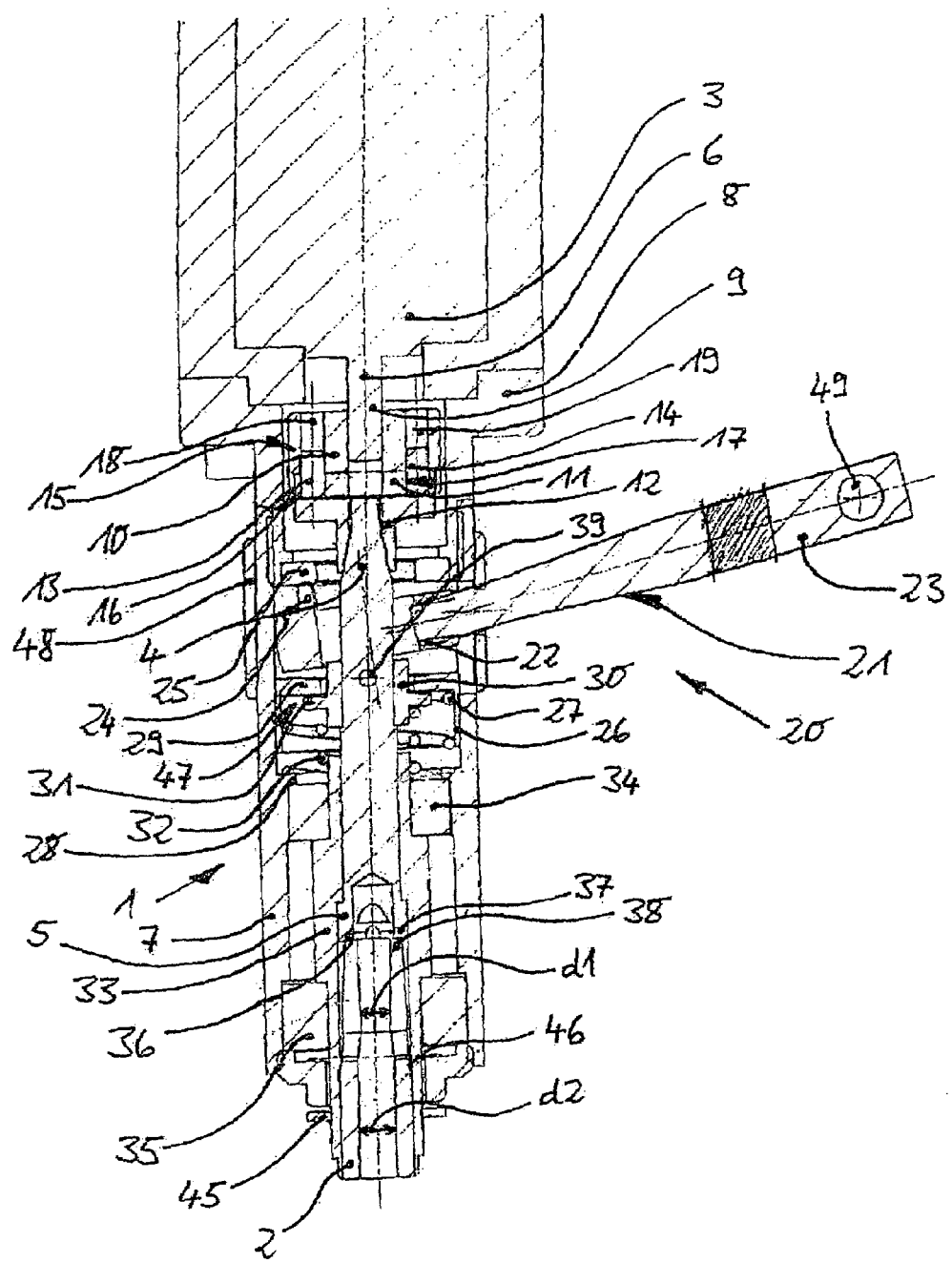
FIG. 1—a sectional view of a tool holder with a drive motor.

Corresponding elements have been designated with the same reference numerals in all of the figures of the drawing.

FIG. 1 is a sectional view of a tool holder 1 configured as a drilling head and milling head for a rotating tool (not shown here) that can be held by a collet chuck 2 of the tool holder 1. The tool holder 1 also has a drive shaft 4 connected to a drive motor 3, for instance, an electric motor or a compressed-air motor or a hydromotor. The collet chuck 2 is positively connected to the drive shaft 4 to transmit torque from the drive motor 3 to the tool, namely, by means of a coupling element 5 in the form of a plunger. The tool is held in a very stable manner between clamping fingers 38 in an end area of the collet chuck 2 facing the drive shaft 4.

In this embodiment, the drive shaft 4 and the coupling element 5 are joined to each other so as to form a single part and the coupling element 5 is part of the drive shaft 4. The coupling element 5 and with it, the drive shaft 4, can be displaced axially relative to the collet chuck 2, in other words, in the direction of a rotational axis 6 of the tool holder 1. During such an axial displacement of the coupling element 5, the tool is loosened in the collet chuck 2. After the tool has been loosened, it can then be removed from the collet chuck 2.

The tool holder 1 also has a housing 7 with a flange part 8 by means of which the drive motor 3 is connected to the tool holder 1. A projection 10 that holds an elastic coupling disk 11 is affixed to a motor driven shaft 9 of the drive motor.

Across from the coupling disk 11 on the motor side, a disk-shaped attachment 12 is affixed on the drive shaft 4 of the tool holder 1 and, together with the projection 10 on the motor driven shaft 9 and two connecting pins 13, 14, said attachment 12 forms a coupling 15 between the motor driven shaft 9 of the drive motor 3 and the drive shaft 4 of the tool holder 1. The connecting pins 13, 14 are affixed to the attachment 12 of the drive shaft 4 of the tool holder 1 and engage with corresponding recesses 16, 17 of the coupling disk 11. Recesses 18, 19 are located in the projection 10 on the motor driven shaft 9 so as to be flush with the recesses 16, 17 of the coupling disk 11.

The tool holder 1 also has an actuation element 20 with a lever 21, said lever 21 being provided with a functional element 22 arranged inside the housing 7 and with a handle section 23 that extends outside of the housing 7. The lever 21 can be actuated manually although it is also conceivable to connect a drive that can be operated pneumatically or else by an electric motor or a hydromotor to a recess 49 of the lever 21 in order to actuate the lever.

The functional element 22 is in the shape of a ring and surrounds the drive shaft 4, said drive shaft 4 being arranged centered relative to the functional element 22. Moreover, the functional element 22 has such a diameter and its outer surface has such a convex curvature that, in every position up to an area where the handle section 23 starts, it lies against the housing 7 of the tool holder 1 along the entire circumference.

A cam 24 is arranged on a side of the functional element 22 facing the drive motor 3. On the motor side, the functional element 22 lies against a stationary ring 25, namely, by means of the cam 24. On the tool side, that is to say, on an opposite side facing away from the drive motor 3, the functional element 22, with another cam that is concealed by the drive shaft 4 here, lies against a cylindrical contact element 26 that can be displaced in the axial direction relative to the rotational axis 6, said contact element 26 being supported on the tool side by a compression spring 27 configured as a helical spring against a protrusion 28 of the housing 7. On a side facing the drive motor 3, the contact element 26 has a ring-shaped shoulder 29 that extends perpendicular to the rotational axis 6.

A cuff 30 with an encircling collar 31 is secured non-rotatably on the drive shaft 4 by means of a pin 39. The collar 31 is oriented parallel to the shoulder 29 of the contact element 26 and is dimensioned in such a way that planar surfaces of the shoulder 29 and of the collar 31 located across from each other come in contact with each other when the contact element 29 is moved towards the end of the tool holder 1 on the tool side. The cuff 30 is supported against a spindle shaft 33 on the tool side by a compression spring 32 configured as a helical spring.

The spindle shaft 33 surrounds a section on the tool side of the drive shaft 4 with the coupling element 5 and the entire collet chuck 2. The spindle shaft 33 is supported in the tool holder 1 by means of two bearings 34, 35 which are configured here as anti-friction bearings and especially as ball bearings, and which are arranged in the housing 7. The bearings 34, 35 have the largest possible distance from each other, which can advantageously result in a better concentric running of the tool.

The collet chuck 2 is arranged in a centered through-recess of the spindle shaft 33 and lies against an axial stop 46 of the spindle shaft 33. Up to the axial stop 46, the collet chuck 2, starting from its end on the tool side, initially has a constant outer diameter and subsequently a continuously decreasing outer diameter, for instance, at an angle of 3°. The collet chuck 2 is pressed and glued into the spindle shaft 33.

When the tool (not shown here) is clamped in the tool holder 1, the lever 21 is in its initial position. In this position, where the functional element 22 of the lever 21 assumes its smallest axial extension, the lever 21 is held by the force of the compression spring 27 that supports the contact element 26, said forced being transmitted by the contact element 26. If the lever 21 is moved into a horizontal position, the axial extension of the functional element 22 increases, as a result of which the moveable contact element 26 is moved towards the end of the tool holder 1 on the tool side. In this process, the two opposing planar surfaces of the shoulder 29 and of the collar 31 come into contact, so that the cuff 30 is also moved.

Since the collar 30 is firmly connected to the drive shaft 4, the drive shaft 4 and the coupling element 5 also move to the end of the tool holder 1 on the tool side. The coupling element 5, which has two wedge-shaped coupling projections 36, 37 that engage with the collet chuck 2, spreads the clamping fingers 38 of the collet chuck 2 apart and releases the tool since the collet chuck 2 is securely arranged in the spindle shaft 33, whereas the drive shaft 4 can be axially displaced together with the coupling element 5 in the spindle shaft 33. In this manner, the tool is loosened due to the axial displacement of the coupling element 5 relative to the collet chuck 2.

When the lever 21 is moved into its loosening position, the connecting pins 13, 14 of the coupling 15 also move towards the end of the tool holder 1 on the tool side. However, the connecting pins 13, 14 do not completely leave the recesses 16, 17 of the coupling disk 11, so that the drive is not uncoupled. Even if the drive motor 3 is not switched off before the lever 21 is actuated, no damage occurs to the tool holder 1 since the surfaces of the contact element 26 and of the cuff 30, which have now come into contact with each other, form the friction elements of a friction coupling 47 that can absorb and/or dissipate the generated friction heat into the environment. The friction coupling 47 is an important safety component. The collet chuck 2 is not loosened from the drive shaft 4. The collet chuck 2 opens, that is to say, the collet chuck 2 either releases a clamped tool or else is ready to receive a tool that will be inserted into the collet chuck 2 when the lever 21 is in a final position that is the loosening position in which preferably the drive motor 3 is also completely braked and—in the case of an electric drive motor 3—is loaded with a high current.

In the end area of the collet chuck 2 facing the drive shaft 4, that is to say, on the motor side here, said collet chuck 2 has a first inner diameter d1 and, in its end area facing away from the drive shaft 4, that is to say, on the tool side, it has a second inner diameter d2 that is larger than the first inner diameter d1.

Furthermore, a disk 45 made of polytetrafluoroethylene (PTFE) protruding radially to the outside is arranged in the end area of the spindle shaft 33 in order to protect the tool holder 1 from dirt. Protection against dirt is also provided by a sleeve 48 that covers a connecting joint area between the actuation element 20 and the drive shaft 4 and that is displaced axially when the lever 21 is actuated.

Figure 2:
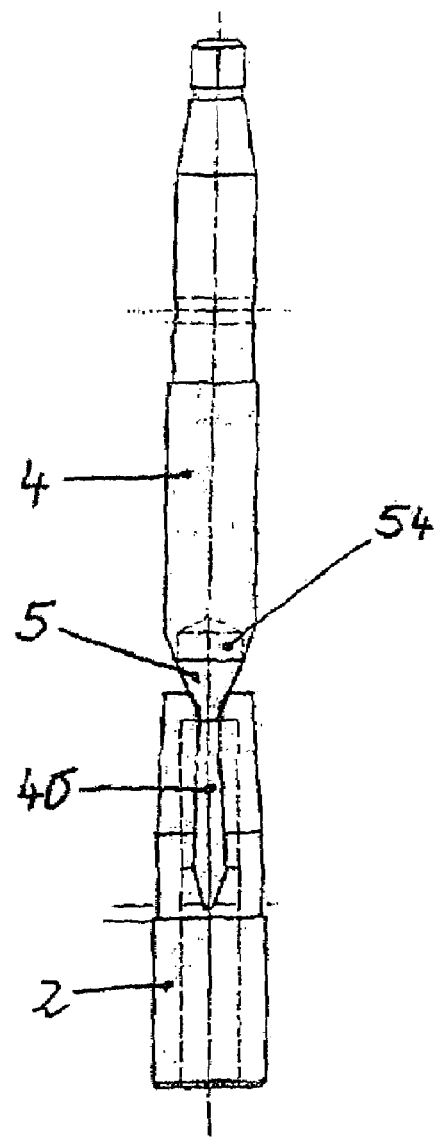
FIG. 2—a side view of a drive shaft with a collet chuck of the tool holder according to FIG. 1, FIG. 3—another side view of the drive shaft with the collet chuck according to FIG. 2, FIG. 4—the collet chuck according to FIGS. 2, 3 in a perspective view, FIG. 5—the collet chuck according to FIGS. 2 to 4 in a side view, FIG. 6—a spindle shaft with a collet chuck, FIG. 7—a sectional view of another tool holder with a drive motor, FIG. 8—a sectional view of a balancing unit of a tool holder, and FIG. 9—a sectional view of an assembly unit of a tool holder.
Figure 3:
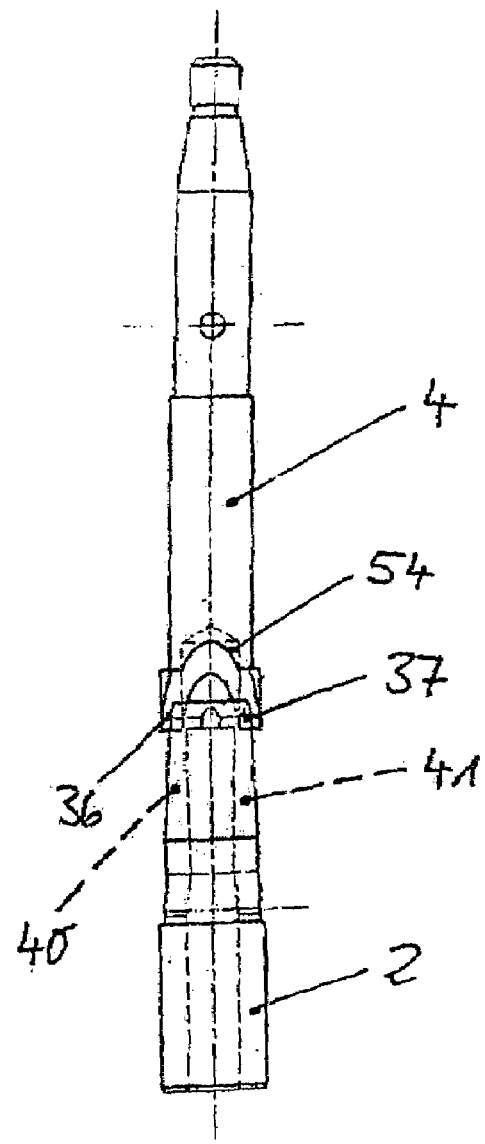

FIGS. 2 and 3 illustrate the configuration of the drive shaft 4 and of the collet chuck 2 as well as the connection of these parts, whereby FIGS. 2 and 3 show side views that are rotated by 90° with respect to each other. The collet chuck 2 has two axially oriented collet chuck slits 40, 41 with each of which a coupling projection 36, 37 of the coupling element 5 connected to the drive shaft is axially engaged.

In the embodiment according to FIGS. 2 and 3, the coupling element 5 has a centered recess 54 in the form of a pocket hole with which the tool can engage. As a result, the coupling element 5 has a forked end with the coupling projections 36, 37 that engages with the collet chuck 2, said projections 36, 37 both being configured like wedges. However, it is likewise conceivable to dispense with the recess 54 so that the end of the coupling element 5 that engages with the collet chuck 2 is configured as a simple, continuous wedge that extends beyond the entire diameter of the collet chuck 2; then the tool can no longer pass through the collet chuck 2 in its full length and engage with the coupling element 5.

Figure 4:
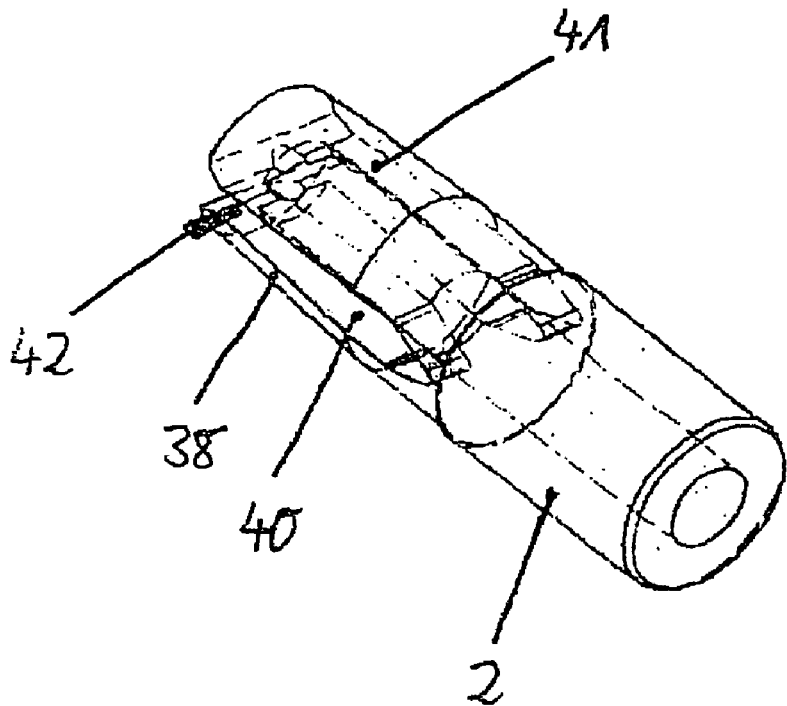

FIG. 4 shows a perspective view of the collet chuck 2. The clamping fingers 38 and the collet chuck slits 40, 41 located between these fingers can be seen here. On the end of the collet chuck 2 facing the drive shaft 4 (see FIG. 1), the collet chuck slits 40, 41 each form a collet chuck opening 42.

Figure 5:
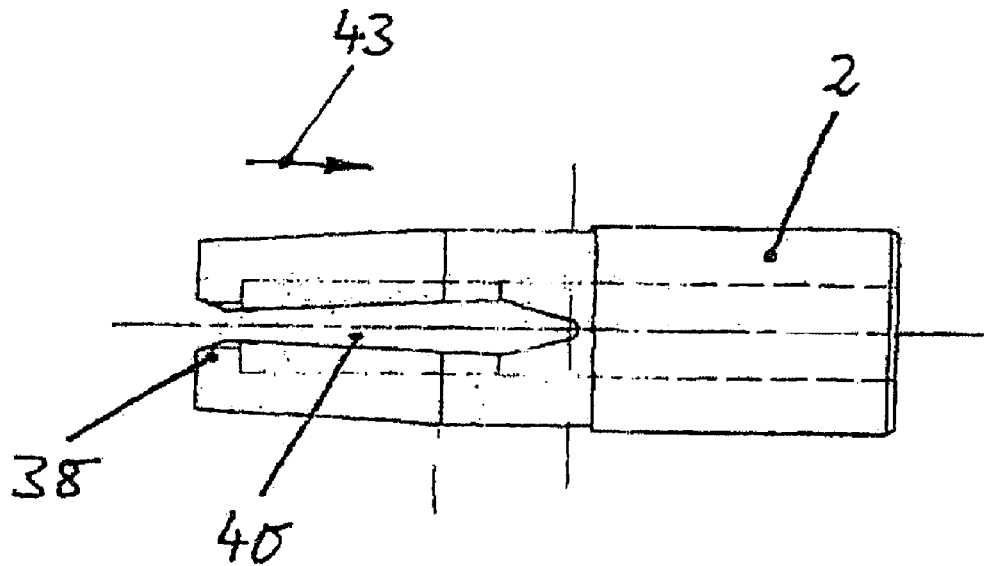

FIG. 5 shows a side view of the collet chuck 2. The collet chuck slit delineated by the clamping fingers 38, of which the collet chuck slit 40 located in the front in this view can be seen, has a slit width that increases in a direction facing away from the drive shaft 4 (see FIG. 1) as indicated by the arrow 43. The clamping fingers 38 clamp the tool uniformly along the entire length. Moreover, by geometrically coordinating the configuration of the clamping fingers 38, the collet chuck 2 can be uniformly opened along the entire length, as a result of which the tool can be easily removed.

Figure 6:
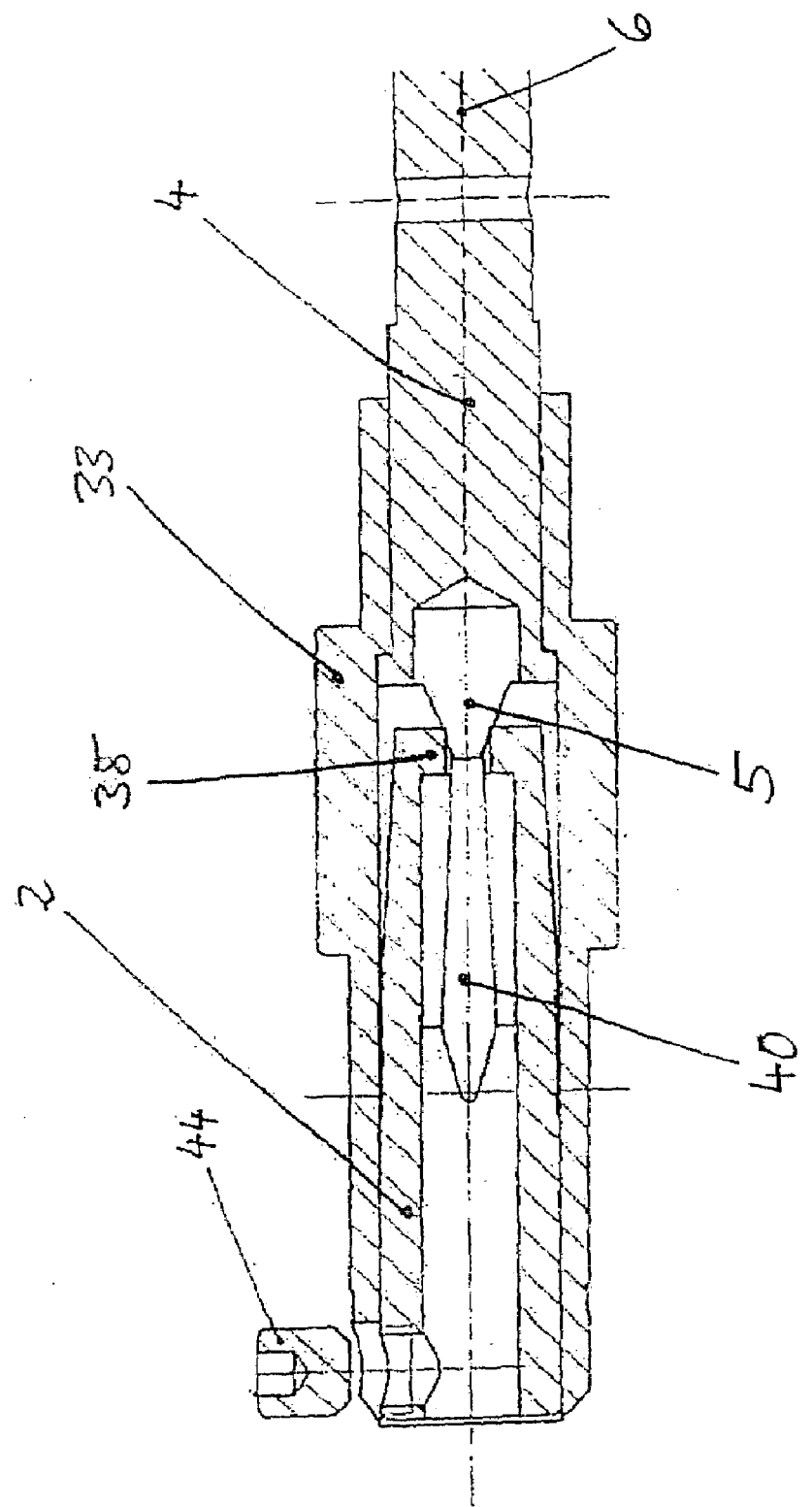

FIG. 6 shows another embodiment in a sectional view. A drive shaft 4 with a coupling element 5 is arranged so as to be axially displaceable in a spindle shaft 33—which can rotate around a rotational axis 6—of a tool holder (not shown here). The coupling element 5 engages axially and between clamping fingers 38 with a collet chuck slit 40 of a collet chuck 2, the latter being securely connected, especially glued, to the spindle shaft 33. In addition, a screw 44 configured as a hexagon socket head screw 44 (Allen screw) is provided for purposes of locking the collet chuck 2 with respect to the spindle shaft 33. Using the screw 44, the pull-out force can be increased, for example, starting from 500 N, to an order of magnitude above 500 N, for example, 700 N to 800 N, which is advantageous, for instance, for machining, particularly for milling aluminum, especially at low speeds. Preferably, another corresponding screw (not shown here) can be provided symmetrically to the screw 44.

Figure 7:
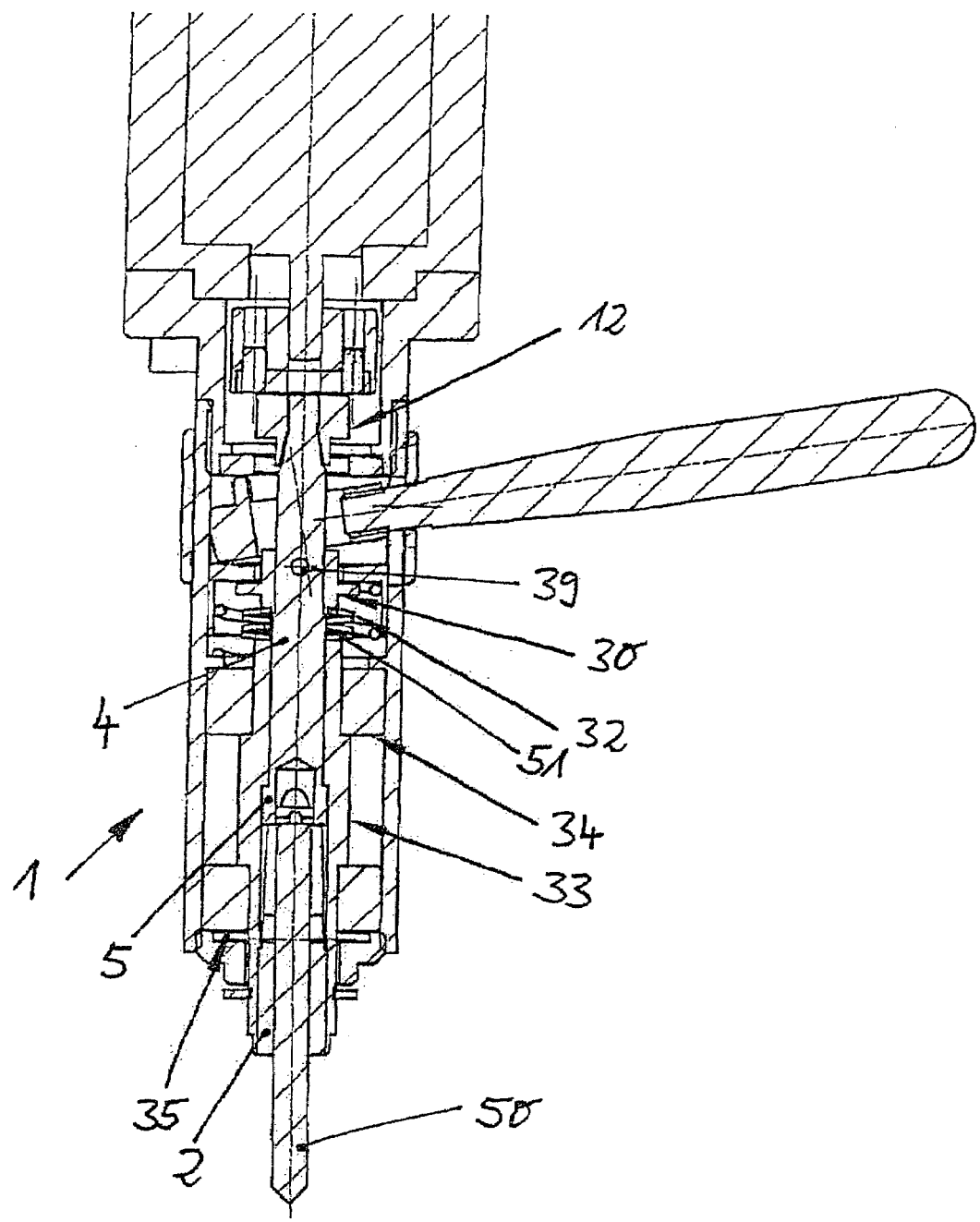

FIG. 7 shows another tool holder 1 with a drive motor 3 in a sectional view. The tool holder has a collet chuck 2 that holds a tool 50. In contrast to the embodiment according to FIG. 1, in the case of the tool holder 1 according to FIG. 7, a cascade-like spring arrangement consisting of disk springs or cup springs 51 is arranged as the compression spring 32 between a cuff 30 and a spindle shaft 33. After the balancing and before the assembly, no more changes have to be made to an assembly and balancing unit comprising the spindle shaft 33 having bearings 34, 35 that are configured as ball bearings, the collet chuck 2, a coupling element 5, a drive shaft 4, the compression spring 32, the cuff 30 with a pin 39 and an attachment 12. The same also applies to the embodiment described above in which the compression spring 32 arranged between the cuff 30 and the spindle shaft 33 is configured as a helical spring (see FIG. 1).

Figure 8:
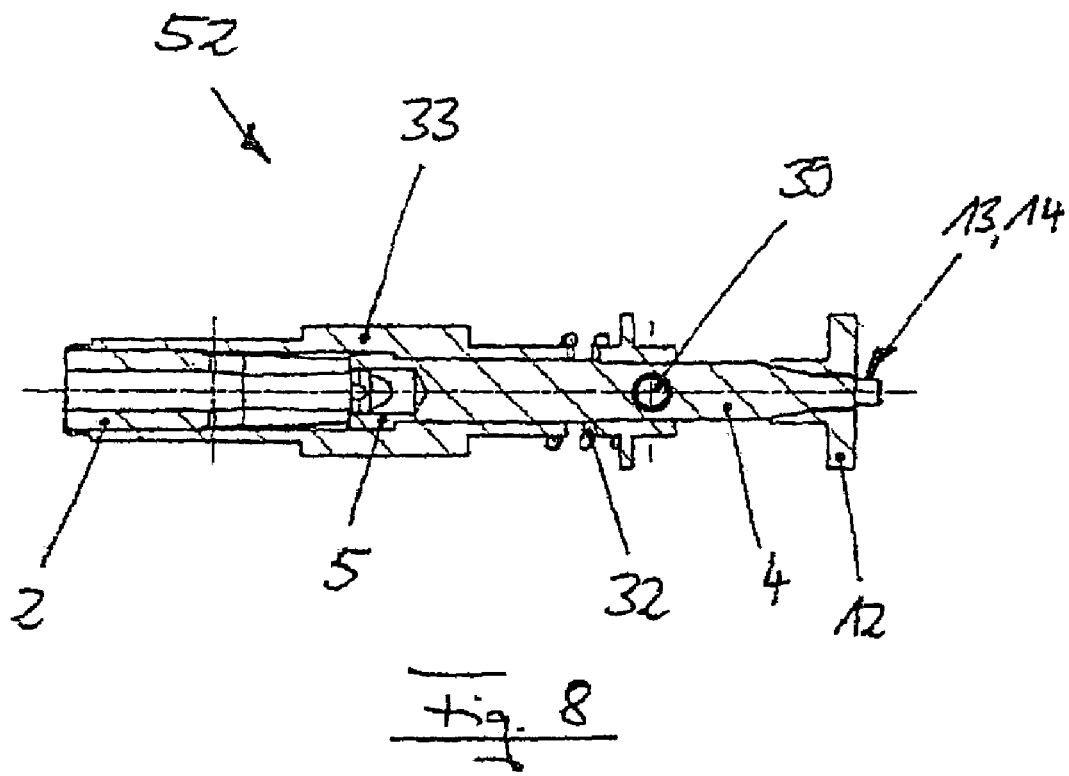

FIG. 8 shows a balancing unit 52 of a tool holder (not shown here). The balancing unit 52 comprises a spindle shaft 33 with a collet chuck 2, a coupling element 5, a drive shaft 4, a compression spring 32 configured as a helical spring, a cuff 30, a pin 39 configured as a hexagon socket head screw (Allen screw) and an attachment 12. This attachment 12 (also see FIG. 1) is provided with connecting pins 13, 14 configured as axial pins. Balancing is of great significance since unbalances regularly present in rotating parts of the tool holder, especially when the tool is operated at high rotational speeds, would otherwise cause the concentric running to be inadequate and lead to increased wear and tear. Balancing compensates for such unbalances.

Figure 9:
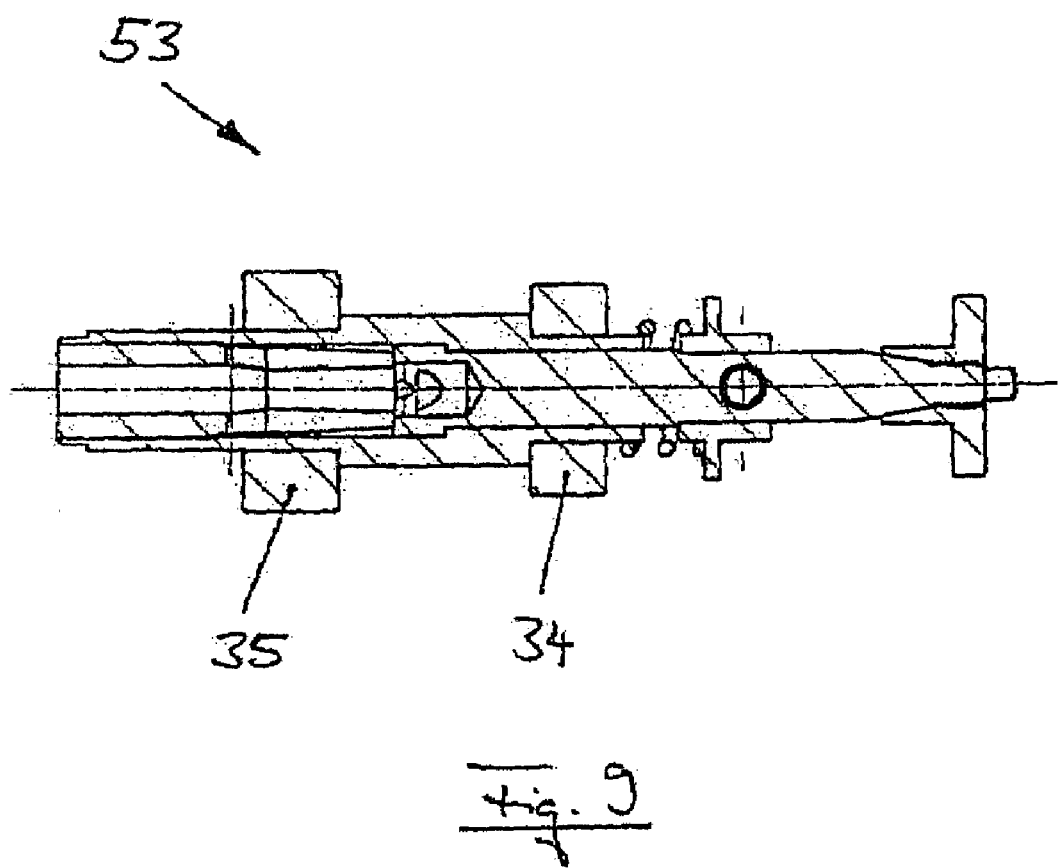

Once the balancing has been completed, bearings 34, 35 in the form of ball bearings are added to the balancing unit, resulting in the assembly unit 53 shown in FIG. 9 for installation into the tool holder. Separating the balancing unit 52 from the assembly unit 53—as provided for in the embodiment according to FIGS. 8, 9—is particularly advantageous in view of cleanliness requirements, since balancing can be performed without the bearings 34, 35.

The invention claimed is:

1. A tool holder for a rotating tool, the tool holder comprising:
    a drive shaft configured to be connected to a drive motor;
    a collet chuck non-rotatably connected to the drive shaft and configured to hold the tool;
    a coupling element positively connecting the drive shaft and the collet chuck so as to transmit torque between the drive shaft and the coupling element, wherein the coupling element is axially displaceable relative to the collet chuck so as to release the tool.

2. The tool holder as recited in claim 1, wherein the drive shaft and the coupling element are joined to each other so as to form a single part.

3. The tool holder as recited in claim 1, wherein the collet chuck includes a first end area facing the drive shaft having a first inner diameter and a second end area facing away from the drive shaft having a second inner diameter larger than the first inner diameter.

4. The tool holder as recited in claim 1, wherein the coupling element has a coupling projection that engages with the collet chuck.

5. The tool holder as recited in claim 4, wherein the coupling projection has a wedge on an end facing the collet chuck.

6. The tool holder as recited in claim 1, wherein the coupling element has a centered recess on an end facing the collet chuck.

7. The tool holder as recited in claim 4, wherein the collet chuck has an axially oriented collet chuck slit and the coupling projection engages with the collet chuck slit.

8. The tool holder as recited in claim 7, wherein the collet chuck slit forms an axial collet chuck opening on an end of the collet chuck facing the drive shaft.

9. The tool holder as recited in claim 7, wherein a width of the collet chuck slit increases in a direction facing away from the drive shaft.

10. The tool holder as recited in claim 1, further comprising a spindle shaft holding the drive shaft and the collet chuck.

11. The tool holder as recited in claim 10, wherein the spindle shaft includes a centered through recess and an axial stop, and wherein the collet chuck is disposed in the centered through-recess and against the axial stop.

12. The tool holder as recited in claim 10, wherein the collet chuck is securely supported in the spindle shaft.

13. The tool holder as recited in claim 12, further comprising a screw locking the collet chuck relative to the spindle shaft.

14. The tool holder as recited in claim 1, further comprising a compression spring counteracting an axial displacement of the coupling element.

15. The tool holder as recited in claim 1, further comprising a friction coupling transmitting an axial force to the coupling element so as to cause an axial displacement of the coupling element.

16. The tool holder as recited in claim 15, wherein the friction coupling includes a first friction element securely connected to the drive shaft and a second friction element capable of being brought into contact with the first friction element and axially displaceable relative to the drive shaft.

17. The tool holder as recited in claim 16, further comprising a compression spring, the first friction element and the second friction element each being supported on a tool side against the compression spring.

18. The tool holder as recited in claim 1, further comprising an actuation element configured to axially displace the coupling element.

19. The tool holder as recited in claim 18, wherein the actuation element is operable using at least one of a manual operation, a pneumatic operation, an electric motor and a hydromotor.

20. The tool holder as recited in claim 19, further comprising an axially moveable sleeve to cover a connecting joint area between the actuation element and at least one of the coupling element and the drive shaft.

21. The tool holder as recited in claim 1, further comprising a motor driven shaft, wherein the drive shaft has a coupling on a motor end of the drive shaft that connects the drive shaft to the motor driven shaft, and wherein the drive shaft and the motor driven shaft are engaged irrespective of an axial displacement of the coupling element.

22. The tool holder as recited in claim 10, further comprising a disk disposed on an end of one of the collet chuck and the spindle shaft and protruding radially, wherein the end is facing away from the drive shaft.

23. The tool holder as recited in claim 22, wherein the disk is made of polytetrafluoroethylene (PTFE).

24. The tool holder as recited in claim 1, wherein the tool is one of a drilling head and a milling head.

* * * * *